United States Patent
Kolattukudy et al.

(10) Patent No.: US 6,562,349 B1
(45) Date of Patent: May 13, 2003

(54) OTITIS MEDIA VACCINE

(75) Inventors: Pappachan E. Kolattukudy, Columbus, OH (US); Lauren O. Bakaletz, Columbus, OH (US); Tatiana Sirakova, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/451,184

(22) Filed: Nov. 29, 1999

Related U.S. Application Data

(62) Division of application No. 08/467,722, filed on Jun. 6, 1995, now Pat. No. 6,030,626, which is a division of application No. 08/065,442, filed on May 18, 1993, now abandoned, and a division of application No. 08/457,997, filed on Jun. 1, 1995, now Pat. No. 5,766,608.

(51) Int. Cl.$^7$ .......................... A61K 39/02; A61K 39/00; A61K 39/116; A61K 39/102; A01N 63/00
(52) U.S. Cl. .................. 424/200.1; 424/93.1; 424/93.2; 424/184.1; 424/185.1; 424/190.1; 424/203.1; 424/234.1; 424/242.1; 424/256.1; 424/258.1; 435/7.3
(58) Field of Search ............................... 424/93.1, 93.2, 424/184.1, 203.1, 242.1, 256.1, 93.4, 185.1, 190.1, 200.1, 234.1, 258.1; 435/7.3, 91.4; 935/24, 65, 88

(56) References Cited

U.S. PATENT DOCUMENTS 4,888,170 A * 12/1989 Curtiss, III .................. 424/93
5,110,908 A * 5/1992 Deich et al. ................. 530/403

FOREIGN PATENT DOCUMENTS

WO 94/26304 11/1994

OTHER PUBLICATIONS

Brinton et al. 1989. Pediatr. Infect. Dis. J. 8(1): S54–S61.*
Kar et al. 1990.*
Bakaletz et al. 1992. Fifteenth Midwinter Research Meeting, Association for Research in Otolaryngology.*
Karasic et al. 1989. Pediatr. Infect. Dis. J. 8:(1): S62–S65.*
Hoepf et al. 1991. Abstracts of the 5th Intern'l. Symposium: Recent Advances in Otitis Media.*
van Ham et al. 1989. EMBO J. 8(11): 3535–3540.*
Janeway et al. 1997. Immunobiology: The Immune System in Health and Disease. pp. 13:26–13:29.*
"Protection Against Histopathological Changes of Tympanic Membrane (TM) and Middle Ear Mucosa (MM) in a Chinchilla Model of Otitis Media by Immunization with Fimbrial Protein Isolated from Nontypable *Haemophilus influenzae* (NTHi) Strain #1128" by L. Bakaletz, et al., American Society for Microbiology, 93rd General Meeting, May 16–20, 1993, Atlanta, Georgia.

"The Effect of Immunization with Fimbrial Protein in a Chinchilla Model of Nontypable *Haemophilus influenzae*–Induced Experimental Otitis Media" by L. Bakaletz, et al., Second Extraordinary International Symposium on Recent Advances in Otitis Media, Mar. 31–Apr. 3, 1993, Oita, Japan.
"An Investigation of the Molecular Basis of the Adhearence of Nontypable *Haemophilus influenzae* to Mucosal Epithelium" by L. Bakaletz, et al., Molecular Biology of Hearing and Deafness Conf., LaJolla, CA, May 1–4, 1992.
"Passive Immunization of Chinchillas with Anti–NTHi Fimbrial Serum and Protection Against Experimental Otitis Media" by L. Bakaletz, et al., Fifth International Symposium, Recent Advances in Otitis Media, May 20–24, 1991, Columbus, Ohio.
"Serological Relatedness of Fimbriae Expressed by NTHi Isolates Recovered from Children with Chronic Otitis Media" by L. Bakaletz, et al., Fifth International Symposium, Recent Advances on Otitis Media, May 20–24, 1991, Columbus, Ohio.
"Isotype Specific Antibody Response Against OMPs and Fimbriae of Nontypable *Haemophilus influenzae* Isolated from Patients with Chronic Otitis Media" by L. Bakaletz, et al., Fifth International Symposium, Recent Advances in Otitis Media, May 20–24, 1991, Columbus, Ohio.
"Immunological Responsiveness of Chinchillas to Isolated Fimbrial Proteins of Nontypable *Haemophilus influenzae* During Experimental Otitis Media" by L. Bakaletz, et al., Eleventh Midwinter Research Meeting, Association for Research in Otolaryngology, Jan. 31—Feb. 4, 1988, Clearwater Beach, Florida.
"Inhibition of Adherence of Nontypable *Haemophilus influenzae* to Human Oropharyngeal Cells", by L. Bakaletz, et al., Twelfth Midwinter Research Meeting, Association for Research in Otolaryngology, Feb. 5–9, 1989, St. Petersburg Beach, Florida.
"Role of Degree of Fimbriation on Ability of Nontypable *Haemophilus influenzae* to Colonize the Nasophrynx and Middle Ears of the Chinchilla" by L. Bakaletz, et al., Thirteenth Midwinter Research Meeting, Association for Research in Otolaryngology, Feb. 4–8, 1990, St. Petersburg Beach, Florida.

(List continued on next page.)

Primary Examiner—Lynette R. F. Smith
Assistant Examiner—JaNa Hines
(74) Attorney, Agent, or Firm—Calfee, Halter & Griswold LLP

(57) ABSTRACT

It has been discovered that a vaccine comprised of fimbrin, a filamentous protein derived from the bacterial surface appendages of non-typable *Haemophilus influenzae* is useful in studying, preventing or reducing the severity of, otitis media. The gene sequence of the DNA coding for fimbrin and the amino acid sequence of fimbrin have also been determined. Vectors containing DNA coding for fimbrin have also been developed, and transformants have been prepared which contain such vectors and which express such DNA and provide a source of pure fimbrin.

4 Claims, 10 Drawing Sheets

OTHER PUBLICATIONS

"Chinchilla Immunological Responsiveness to Isolated Outer Membrane and Fimbrial Proteins of Nontypable *Haemophilus influenzae*" by L. Bakaletz, et al., Thirteenth Midwinter Research Meeting, Association for Research in Otolaryngology, Feb. 4–8, 1990, St. Petersburg Beach, Florida.

"Colonization of the Chinchilla Middle Ear and Nasopharynx by Fimbriated Isolates of Nontypable *Haemophilus influenzae*" by L. Bakaletz, et al., 90th Annual Meeting of the American Society for Microbiology, May 13–17, 1990, Anaheim, California.

"Presumptive Identification of the NTHi Adhesin for Human Oropharyngeal and Chinchilla Middle Ear Epithelial Cells" by L. Bakaletz, et al., Fifth International Symposium, Recent Advances in Otitis Media, May 20–24, 1991, Columbus, Ohio.

"Inhibition of Adherence to NTHi to Human Oropharyngeal Cells—An Elisa Assay" by L. Bakaletz, et al., Fifth International Symposium, Recent Advances in Otitis Media, May 20–24, 1991, Columbus, Ohio.

"Cloning and Sequencing of a Pilin Gene from NTHi Strain #1128" by L. Bakaletz, et al., Fifth International Symposium, Recent Advances in Otitis Media, May 20–24, 1991, Columbus, Ohio.

"Protection of Chinchillas Against Experimental Otitis Media via Active Immunization with NTHi Strain #1128 Fimbrin" by L. Bakaletz, et al., Fifteenth Midwinter Research Meeting, Association for Research in Otolaryngology, Feb. 2–6, 1992, St. Petersburg, Florida.

"Frequency of Fimbriate Isolates of Nontypable *Hoemophilus influenzae* from the Middle Ears and Nasopharynges of Patients with Chronic Media" by L. Bakaletz, et al., Proceedings of the Fourth International Symposium, Recent Advances in Otitis Media, Jun. 1987, Columbus, Ohio, pp. 331–335.

"Evaluation of pilus vaccines for prevention of experimental otitis media caused by notypable *Haemophilus influenzae*" by R. Karasic, et al., *Pediatr Infect Dis J.*, vol. 8, No. 1, Jan. 1989, pp. S62–S65.

"Cloning and Expression in *Escherichia coli* of LKP Pilus Genes from a Nontypeable *Hoemophilus influenzae* Strain" by S. Kar, et al., *Infection and Immunity*, vol. 58, No. 4, Apr. 1990, pp. 903–908.

"Design and development of pilus vaccines for *Haemophilus influenzae* diseases" by C. Brinton, et al., *Pediatr Infect Dis J.*, vol. 8, No. 1, Jan. 1989, pp. S54–S61.

"Passive immunization of chinchillas against experimental otitis media with anti–NTHi fimbrial subunit (fimbrin) sera" by L. Bakaletz, et al., 91st General Meeting of the American Society for Microbiology, May 5–9, 1991, Dallas, Texas.

"Somatic antigens of *Haemophilu influenzae* as vaccine components" by T. Murphy, et al., *Pediatr Infect Dis J*, vol. 8, No. 1, Jan. 1989, pp. S66–S68.

"Loss of Capsule Expression by *Haemophilu influenzae* Type b Results in Enhanced Adherence to and Invasion of Human Cells" by J. St. Geme, et al., *Infection and Immunity*, vol. 59, N. 4, Apr. 1991, pp. 1325–1333.

"*Haemophilus influenzae* Adheres to and Enters Cultured Human Epithelial Cells" by J. St. Geme, et al., *Infection and Immunity*, vol. 58, No. 12, Dec. 1990, pp. 4036–4044.

"Comparison of Hemagglutinating Pili of *Haemophilus influenzae* Type b with Similar Structures of Nontypeable *H. influenzae*" by J. Gilsdorf, et al., *Infection and Immunity*, vol. 60, No. 2, Feb. 1992, pp. 374–379.

"Effect of Pili–Specific Antibodies on the Adherence of *Haemophilus influenzae* Type b to Human Buccal Cells" by L. Forney, et al., *The Journal of Infectious Diseases*, Mar. 1992, vol. 165, pp. 464–470.

"Inability To Express Fimbriae Results in Impaired Ability of *Haemophilus influenzae* b To Colonize the Nasopharynx" by A. Weber, et al., *Infection and Immunity*, vol. 59, No. 12, Dec. 1991, pp. 4724–4728.

"Interaction of Nontypable *Haemophilus influenzae* with Human Respiratory Mucosa In Vitro" by R. Read, et al., *The Journal of Infectious Diseases*, Mar. 1991, vol. 163, pp. 549–558.

"Characterization of Antigens from Nontypable *Haemophilus influenzae* Recognized from Human Bactericidal Antibodies" by H. Gnehm, et al., *J. Clin. Invest.*, vol. 75, May 1985, pp. 1646–1658.

"Modifications of Otitis Media in Chinchillas Rechallenged with Nontypable *Haemophilu influenzae* and Serological Response to Outer Membrane Antigens" by R. Karasic, et al., *The Journal of Infectious Diseases*, vol. 151, No. 2, Feb. 1985, pp. 273–279.

"Development of serum bactericidal activity following nontypable *Haemophilus influenzae* acute otitis media" by S. Barenkamp, et al., *Pediatr Infect Dis J*, vol. 9, No. 5, May 1990, pp. 333–339.

"Protection by Serum Antibodies in Experimental Nontypable *Haemophilus influenzae* Otitis Media" by S. Barenkamp, et al., *Infection and Immunity*, vol. 52, No. 2, May 1986, pp. 572–578.

"Nontypable *Haemophilus influenzae*: A Review of Clinical Aspects, Surface Antigens, and the Human Immune Response to Infection" by T Murphy, et al., *Reviews of Infectious Diseases*, vol. 9, No. 1, Jan.–Feb. 1987, pp. 1–13.

"Comparison and Analysis of the Nucleotide Sequences of Pilin Genes from *Haemophilu influenzae* Type b Strains Eagan and M43" by L. Forney, et al., *Infection and Immunity*, vol. 59, No. 6, Jun. 1991, pp. 1991–1996.

"Purification and Partial Characterization of Outer Membrane Proteins P5 and P6 from *Haemophilus influenzae* Type b" by R. Munson, Jr., et al., *Infection and Immunity*, vol. 49, No. 3, Sep. 1985, pp. 544–549.

"Evaluation of Mixtures of Purified *Haemophilus influenzae* Outer Membrane Proteins in Protection against Challenge with Nontypable *H. Influenzae* in the Chinchilla Outer Media Model" by B. Green, et al., *Infection and Immunity*, vol. 61, No. 5, May 1993, pp. 1950–1957.

"The e (P4) Outer Membrane Protein of *Haemophilus influenzae*: Biologic Activity of Anti–e Serum and Cloning and Sequencing of the Structural Gene" by B. Green, et al., *Infection and Immunity*, vol. 59, No. 9, Sep. 1991, pp. 3193–3198.

"Frequency of Fimbriation of Nontypable *Haemophilus influenzae* and Its Ability to Adhere to Chinchilla and Human Respiratory Epithelium" by L. Bakaletz, et al., *Infection and Immunity*, vol. 56, No. 2, Feb. 1988, pp. 331–335.

"Immunological Responsiveness of Chinchillas to Outer Membrane and Isolated Fimbrial Proteins of Nontypable *Haemophilus influenzae*" by L. Bakaletz, et al., *Infection and Immunity*, vol. 57, No. 10, Oct. 1989, pp. 3226–3229.

"Serum and Middle Ear Antibody Response in the Chinchilla during Otitis Media with Effusion Induced by Nonviable Nontypable *Hoemophilus influenzae*" by T. DeMaria, et al. *The Journal of Infectious Disease*, Jun. 1992, vol. 165, Supplement 1, pp. S196–S197.

Abstract P696, "Peptides in Immunology/Cancer Vaccines" Fourteenth American Peptide Symposium, Jun. 18–23, 1995, Columbus, Ohio, p. 2–176.

"Use of Synthetic Peptides of Fimbrin Isolated from NTHi Strain #1128 as Immunogens in Rabbits and Chinchillis" by L. Bakaletz, Sixth International Symposium on Recent Advances in Otitis Media, Jun. 4–8, 1995, Fort Lauderdale, Florida.

Abstract S9, "The Importance of Microbial Immunity Determinants in Protection Against Otitis Media" By L. Bakaletz, 6th International Congress of Pediatric Otorhinolaryngolgoy, May 29–Jun. 1, 1994, Rotterdam.

"Modeling Adenovirus Type 1–Induced Otitis Media in the Chinchilla: Effect on Ciliary Activity and Fluid Transport Function of Eustachian Tube Mucosal Epilthelium" by L. Bakaletz, et al., *The Journal of Infectious Diseases*, vol. 168, 1993, pp. 865–872.

"Synergistic Effect of Adenovirus Type 1 and Nontypable *Haemophilus influenzae* in a Chinchilla Model of Experimental Otitis Media" by K. Suzuki, et al., *Infection and Immunity*, vol. 62, No. 5, May 1994, pp. 1710–1718.

"De Novo" Engineering of Peptide Immunogenic and Antigenic Determinants as Potential Vaccines by P. Kaumaya, *Peptides: Design, Synthesis, and Biological Activity*, 1994, pp. 133–164.

"Molecular Cloning and Sequencing of the Gene for Outer Membrane Protein P5 of *Haemophilus influenzae*" by R. Munson, Jr., et al., *Infection and Immunity*, vol. 61, No. 9, Sep. 1993. pp. 4017–4020.

"Chapter 100: Measles" by C. Sullivan, et al., *Infectious Diseases, Fifth Edition*, J.B. Lippincott Company, Philadelphia, 1994, pp. 892–902.

Abstract 179 "Protection of Chinchillas Against Experimetal Otitis Media Following Passive Immunization with Anti–NTHI Fimbrial Serum" by Bakaletz, et al., Fourteenth Midwinter Research Meeting, Association for Research in Otolaryngology, Feb. 3–7, 1991, St. Petersburg Beach, Florida.

* cited by examiner

Fig. 5A

```
  1 atgtcactgaggatgcgattagacctggccacatgctattaactcattaagctaaaatgg  60
 61 cagctcattgacctaatatcttaaggcgttaatgatgtcgaattagattttgagcattta 120
121 agagtgtttatggagaaatgatgcaagaaagtgtgtgtttggatgttttcaataacaaaa 180
181 attcaaaagatatgatcttttcaattttataggataataagcgcacttttgaacgttcct 240
241 ttggggtaaacataaacaaaggaattgaatttgtcaaaaggtagcaatgaggcaaattca 300
301 aaccctcgttaagtgaactgtttagaagataactttgattaaaagttcggtctaaacggg 360
361 aataattttttattactattcgatgactaaatagaggacatcaaa ATG AAA AAA     414
```

```
  1                                                    M   K   K    3
415 ACT GCA ATC GCA TTA GTA GTT GCT GGC TTA GCA GCA GCT TCA GTA 459
  4  T   A   I   A   L   V   V   A   G   L   A   A   A   S   V  18

460 GCT CAA GCA GCT CCA CAA GAA AAT ACT TTC TAC GCT GGC GTT AAA 504
 19  A   Q   A   A   P   Q   E   N   T   F   Y   A   G   V   K  33

505 GCT GGT CAA GGA TCT TTC CAT GAT GGT ATT AAC AAT AAT GGC GCA 549
 34  A   G   Q   G   S   F   H   D   G   I   N   N   N   G   A  48

550 ATT AAA AAG GGA TTA TCA TCT AGT AAT TAT GGT TAC AGA CGC AAT 594
 49  I   K   K   G   L   S   S   S   N   Y   G   Y   R   R   N  63

595 ACT TTC ACT TAT GGT GTA TTT GGT GGT TAC CAA ATT TTA AAT CAA 639
 64  T   F   T   Y   G   V   F   G   G   Y   Q   I   L   N   Q  78

640 GAT AAT TTT GGT TTA GCT GCT GAA TTA GGT TAC GAC GAT TTC GGT 684
 79  D   N   F   G   L   A   A   E   L   G   Y   D   D   F   G  93

685 CGT GCA AAA CTT CGT GAA GCG GGA AAA CCT AAA GCT AAA CAT ACT 729
 94  R   A   K   L   R   E   A   G   K   P   K   A   K   H   T 108

730 AAC CAC GGT GCG TAC TTA AGC TTA AAA GGC AGC TAT GAA GTG TTA 774
109  N   H   G   A   Y   L   S   L   K   G   S   Y   E   V   L 123

775 GAC GGT TTA GAT GTT TAT GGC AAA GCA GGT GTT GCT TTA GTA CGT 819
124  D   G   L   D   V   Y   G   K   A   G   V   A   L   V   R 138

820 TCT GAT TAT AAA TTT TAT GAA GAT GCA AAC GGT ACT CGT GAC CAC 864
139  S   D   Y   K   F   Y   E   D   A   N   G   T   R   D   H 153

865 AAG AAA GGT CGT CAC ACA GCA CGT GCC TCT GGT TTA TTT GCA GTA 909
154  K   K   G   R   H   T   A   R   A   S   G   L   F   A   V 168
```

MATCH TO FIG. 5B

MATCH TO FIG. 5A

```
910  GGT GCA GAA TAC GCA GTA TTA CCA GAA TTA GCA GTT CGT TTA GAA  954
169  G   A   E   Y   A   V   L   P   E   L   A   V   R   L   E   183

955  TAC CAA TGG CTA ACT CGC GTA GGT AAA TAC CGC CCT CAA GAT AAA  999
184  Y   Q   W   L   T   R   V   G   K   Y   R   P   Q   D   K   198

1000 CCA AAT ACC GCA ATT AAC TAC AAC CCT TGG ATT GGT TGT ATC AAA  1044
199  P   N   T   A   I   N   Y   N   P   W   I   G   C   I   N   213

1045 GCG GGT ATT TCT TAC CGT TTC GGT CAA GGC GAA GCA CCA GTT GTT  1089
214  A   G   I   S   Y   R   F   G   Q   G   E   A   P   V   V   228

1090 GCA GCA CCT GAA ATG GTA AGC AAA ACT TTC AGC TTA AAT TCT GAT  1134
229  A   A   P   E   M   V   S   K   T   F   S   L   N   S   D   243

1135 GTA ACT TTC GCA TTT GGT AAA GCA AAC TTA AAA CCT CAA GCA CAA  1179
244  V   T   F   A   F   G   K   A   N   L   K   P   Q   A   Q   258

1180 GCT ACA TTA GAC AGC GTC TAT GGC GAA ATT TCA CAA GTT AAA AGT  1224
259  A   T   L   D   S   V   Y   G   E   I   S   Q   V   K   S   273

1225 CGA AAA GTA GCT GTT GCT GGT TAC ACT AAC CGT ATT GGT TCT GAC  1269
274  R   K   V   A   V   A   G   Y   T   N   R   I   G   S   D   288

1270 GCG TTC AAC GTA AAA CTT TCT CAA GAA CGT GCA GAT TCA GTA GCT  1314
289  A   F   N   V   K   L   S   Q   E   R   A   D   S   V   A   303

1315 AAC TAC TTT GTT GCT AAA GGT GTT GCA GCA GAC GCA ATC TCA GCA  1359
304  N   Y   F   V   A   K   G   V   A   A   D   A   I   S   A   318

1360 ACT GGT TAC GGT GAA GCA AAC CCA GTA ACT GGC GCA ACT TGT GAC  1404
319  T   G   Y   G   E   A   N   P   V   T   G   A   T   C   D   333

1405 CAA GTT AAA GGT CGT AAA GCA CTT ATC GCT TGT CTT GCT CCA GAC  1449
334  Q   V   K   G   R   K   A   L   I   A   C   L   A   P   D   348

1450 CGT CGT GTA GAA ATC GCA GTA AAC GGT ACT AAA TAA ttttagtcgttt  1497
349  R   R   V   E   I   A   V   N   G   T   K                    360

1498      aacgaaagattaaatacaggaaaaggcttaaacttcggtttaggccttttgttttaaacg 1557
1558 aaactaaaaccaagcattttaatcaagtttttaacttgtgataaaatgcttacctcgttta 1617
1618 tttataggaaacattatggaaaccttagacaaaatcaaaaaaagcaaattagtgaaaacc 1677
1678 ccattcttatttatatgaaaggttcgccaaaaagtttccatcct                   1720
```

Fig. 5B

OTITIS MEDIA VACCINE

This application is a divisional of the commonly assigned, U.S. patent application Ser. No. 08/467,722 filed Jun. 6, 1995, which issued as U.S. Pat. No: 6,030,626; on Feb. 29, 2000, and which was a divisional of the commonly assigned, U.S. patent application Ser. No. 08/065,442 filed May 18, 1993, now abanonded, and is related to the commonly assigned, divisional U.S. patent application Ser. No. 08/457,997, filed Jun. 1, 1995, now U.S. Pat. No. 5,766,608.

This invention was made with government support in part under Grant No. DC00090 awarded by the National Institute of Health. The government has certain rights in this invention.

BACKGROUND OF THE INVENTION

Otitis media is an infection of the middle ear that occurs primarily in children. Left untreated, the disease can result in hearing loss, and developmental delays. It is estimated that otitis media accounted for 31 million of the 130 million office visits for respiratory diseases in the period from 1987-87. Recent data indicate that suppurative and unspecified otitis media rank first in the list of the 30 most common diagnoses requiring a physician's office visit for patients up to age 24. Over one billion dollars per year is spent on treatment of this disease and the related loss of income for working parents is estimated to be between $300 and $600 million. Approximately 83% of all children by three years of age will have had at least one episode of acute otitis media. Non-typable strains of *Haemophilus influenzae* account for 25–30% of all cases of otitis media, 53% of recurrent otitis media, and are the primary pathogens isolated from 62% of cases of chronic otitis media with effusion. Although non-typable *Haemophilus influenzae* (NTHi) are primary pathogens in otitis media, neither the pathogenic mechanisms nor the host immunological response has been fully defined for this disease.

It would be desirable to have a vaccine to confer immunity to non-typable *Haemophilus influenzae* or to reduce the severity of otitis media caused by *Haemophilus influenzae*.

SUMMARY OF THE INVENTION

It has been discovered that a vaccine comprised of fimbrin, a filamentous protein derived from the bacterial surface appendages of non-typable *Haemophilus influenzae* is useful in studying, preventing or reducing the severity of, otitis media. The gene sequence of the DNA coding of fimbrin and the amino acid sequence of fimbrin have also been determined. Vectors containing DNA coding for Fimbrin have also been developed, and transformants have been prepared which contain such vectors and which express such DNA and provide a source of pure fimbrin.

BRIEF DESCRIPTION OF THE FIGURES

FIG. 4A is a transmission electron micrograph of epon-embedded and thin sectioned NTHi strain #1128 showing thin, filamentous peritrichously arranged fimbriae.

FIG. 5 is the nucleotide sequence of NTHi fimbrin gene (SEQ. ID. NO. 1). The deduced amino acid sequence is shown below the DNA sequence. Capital letters correspond to the open reading frame. Amino acid sequences of the amino terminus and an internal CNBr fragment determined by sequencing of the fimbrin protein are single underlined. The ribosome binding site is double underlined. A stem-loop structure located downstream of the fimbrin gene is in boldface and underlined.

DETAILED DESCRIPTION OF THE INVENTION

It has been found that fimbriae, which are surface appendages, are produced by 100% of the bacteria recovered from the middle ears and nasopharynges of children with chronic otitis media. Fimbriae appear, via transmission electron microscopy, to be involved in the initial docking or adherence of the bacterial cell to mucosal epithelium.

It has also been discovered that vaccinating animals with fimbrin, a protein that comprises fimbriae, induces an immune response to the fimbrin protein, and protects the vaccinated animal from severe otitis media upon subsequent exposure to NTHi.

Immunogold Localization of Fimbriae

Figure 4:
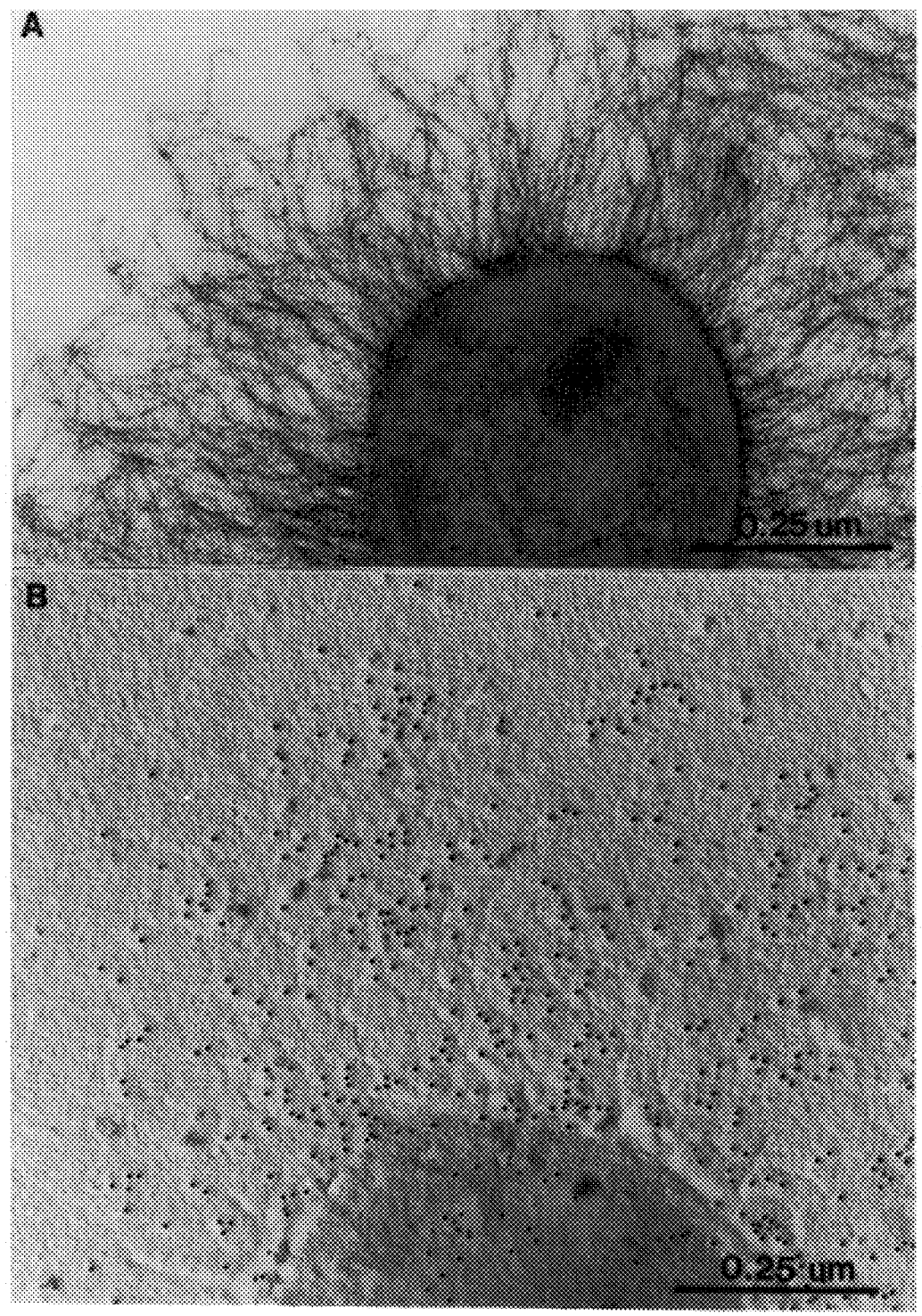
FIG. 4 (B) is a transmission electron micrograph of unfixed, unstained NTHi strain #1128 which has been indirectly immunolabeled with chinchilla anti-fimbrin protein antisera and gold-conjugated protein A and shadow cast. Fimbriae appear as white "rivulets" labeled with black gold spheres.

Unfixed, unstained, immunogold-labeled whole bacteria were subjected to low angle platinum-palladium shadow casting to impart a sense of height to the micrograph in an attempt to more clearly resolve labeling of the low-profile NTHi fimbriae with both a battery of polyclonal and singular monoclonal antibody, designated as MAb 4A5u, directed against the isolated fimbrin protein. As shown in FIG. 4, NTHi strain #1128, American type Culture Collection, (ATCC) Number 55430 was labelled with a pool of chinchilla sera collected from a cohort immunized with the isolated fimbrin protein. Such labelling indicated that the immunological response in chinchillas immunized with isolated fimbrin protein was directed against the fimbriae described on 100% of otitis media isolates examined.

Passive Immunization

The protection conferred by an animal's immune response directed against the fimbrin subunit protein was determined in a chinchilla model of experimental otitis media. Chinchillas were passively immunized with 5 ml/kg hyperimmune chinchilla or rabbit serum directed against fimbrin protein isolated from NTHi strain 1128. Control chinchillas received normal rabbit serum or normal chinchilla serum. Next the chinchilla received transbullar challenge with the homologous NTHi, that is, 2.5 to 3.5 cfu/ear of NTHi strain #1128. The chinchillas were examined and rated. As shown in Table 1, the immunized chinchillas receiving immune rabbit or chinchilla serum displayed reduced tympanic membrane pathology ($p \leq 0.05$ and 0.001 respectively). As shown in Table 2, the presence of middle ear fluids in chinchillas receiving chinchilla anti-fimbrin protein serum were reduced when compared to controls.

TABLE 1

Intensity of Otoscopically Determined Tympanic Membrane Pathology in Passively Immunized Chinchillas Post-Intrabullar Challenge with NTHi

| Group | Antisera 5 ml/kg | | 1 | 2 | 3* | 4 | 5 | 6 | 7* | 8 | 9 | 10* | 11 | 12 | 13 | 14* | 15 | 16 | 17* | 18 | 19 | 20 | 21 |
|---|---|---|---|---|---|---|---|---|---|---|---|---|---|---|---|---|---|---|---|---|---|---|---|
| A | Rabbit anti-NTHi Fimbrial Subunits 1:10 | Left | 1+ | 1+ | 1+ | − | − | 2+ | 2+ | 2+ | 2+ | 2+ | − | − | 2+ | 2+ | 1+ | 1+ | 1+ | − | − | 1+ | 1+ |
| | | Right | 0 | 0 | 0 | − | − | 0 | 1+ | 0 | 0 | 0 | − | − | 0 | 0 | 0 | 0 | 0 | − | − | 0 | 0 |
| B | Rabbit anti-Fimbrial Subunits 1:100 | Left | 1+ | − | 2+ | 1+ | 2+ | 2+ | 1+ | − | − | 3+ | − | − | 3+ | 3+ | − | − | 3+ | − | − | 1+ | 1+ |
| | | Right | 0 | − | 0 | 0 | 0 | + | 0 | − | − | 1+ | − | − | 1+ | 0 | − | − | 0 | − | − | 1+ | 1+ |
| C | Normal Rabbit Serum Undiluted | Left | 2+ | 3+ | 2+ | 3+ | 3+ | 2+ | 2+ | 2+ | 3+ | 2+ | 1+ | − | 1+ | 2+ | 3+ | 3+ | 2+ | 1+ | 1+ | 2+ | 2+ |
| | | Right | 0 | 0 | 0 | 1+ | 1+ | − | 1+ | 0 | 0 | 0 | 1+ | − | 0 | 0 | 1+ | 0 | 0 | 0 | 0 | 0 | 0 |
| D | Normal Rabbit Serum 1:100 | Left | 2+ | 2+ | 2+ | − | − | 2+ | 2+ | 2+ | 3+ | 1+ | − | − | 1+ | 1+ | + | 0 | 0 | − | − | 1+ | 1+ |
| | | Right | 0 | 1+ | 1+ | − | − | 1+ | 2+ | 1+ | 1+ | 1+ | − | − | 1+ | 1+ | 0 | 0 | 0 | − | − | 0 | 0 |
| E | Chinchillas anti-NTHi Fimbrial Subunits Undiluted | Left | 1+ | 1+ | 1+ | 1+ | 0 | 0 | 0 | − | − | 0 | 0 | 1+ | 0 | 0 | − | − | 0 | 0 | 0 | 0 | 0 |
| | | Right | 0 | 1+ | 0 | 0 | 0 | 0 | 0 | − | − | 0 | 0 | 0 | 0 | 0 | − | − | 0 | 0 | 0 | 0 | 0 |
| F | Chinchilla anti-Fimbrial Subunits 1:100 | Left | 1+ | 1+ | 1+ | 1+ | 1+ | 1+ | 1+ | − | − | 0 | 0 | 0 | 0 | 0 | − | − | 0 | 0 | 0 | 0 | 0 |
| | | Right | 0 | 1+ | 1+ | 0 | 0 | 0 | 0 | − | − | 0 | 0 | 0 | 0 | 0 | − | − | 0 | 0 | 0 | 0 | 0 |

TABLE 1-continued

Intensity of Otoscopically Determined Tympanic Membrane Pathology in Passively Immunized Chinchillas
Post-Intrabullar Challenge with NTHi

| Group | Antisera 5 ml/kg | | Days Post-Intrabullar Challenge(a) | | | | | | | | | | | | | | | | | | | |
|---|---|---|---|---|---|---|---|---|---|---|---|---|---|---|---|---|---|---|---|---|---|---|
| | | | 1 | 2 | 3* | 4 | 5 | 6 | 7* | 8 | 9 | 10* | 11 | 12 | 13 | 14* | 15 | 16 | 17* | 18 | 19 | 20 | 21 |
| G | Normal Chinchilla Serum Undiluted | Left | 2+ | 2+ | 2+ | 2+ | 1+ | 1+ | 1+ | – | – | 1+ | 1+ | 1+ | 1+ | 1+ | – | – | 0 | 0 | 0 | 0 | 0 |
| | | Right | 1+ | 0 | 1+ | 1+ | 1+ | 1+ | 0 | – | – | 0 | 0 | 0 | 0 | 0 | – | – | 0 | 0 | 0 | 0 | 0 |

*Epitympanic tap performed post-otoscopy on these days.
(a)Degree of pathology was graded on a 0 to 4+ scale, with 0 = normal drum appearance and 4+ = severe pathology, perforated drum with discharge. Number shown is average for each group.
Group A, B, E–G had 5 animals each.
Group C & D had 4 animals each.

TABLE 2

Presence of Middle Ear Fluids (MEF) in Chinchillas Receiving NCS or CαF Serum

| Days Post-Inoculation | Presence of MEF in Challenged Ears # pos. ears/total | | |
|---|---|---|---|
| | NCS UD | CαF UD | CαF 1:100 |
| 1 | 5/5 | 4/5 | 3/5 |
| 2 | 5/5 | 3/5 | 1/5 |
| 3 | 5/5 | 2/5 | 0/5 |
| 4 | 5/5 | 0/5 | 1/5 |
| 5 | 5/5 | 0/5 | 0/5 |
| 6 | 5/5 | 0/5 | 1/4(a) |
| 7 | 5/5 | 0/5 | 1/4 |
| 10 | 5/5 | 0/5 | 0/4 |
| 11 | 5/5 | 0/5 | 0/4 |
| 12 | 1/5 | 0/5 | 1/4 |
| 13 | 3/5 | 0/5 | 0/4 |
| 14 | 1/5 | 0/5 | 0/4 |
| 17 | 0/5 | 0/5 | 0/4 |
| 18 | 0/5 | 0/5 | 0/4 |
| 19 | 0/5 | 0/5 | 0/4 |
| 20 | 0/5 | 0/5 | 0/4 |
| 21 | 0/5 | 0/5 | 0/4 |

(a)One animal died of undeterminate cause
NCS: normal chinchilla serum
CαF: chinchilla anti-fimbrial serum
UD: undiluted To prepare vaccines for active immunization to NTHi, several NTHi proteins were isolated: the fimbrin protein from NTHi strain 1128; the fimbrin protein from NTHi strain 1885 ATCC Number 55431 and the total outer membrane protein from NTHi strain 1128. While NTHi strains 1128 and 1885 have been described herein, other nontypable *Haemophilus influenzae* strains may be used including the publicly available strains publicly available from the ATCC number 43041.

Isolation of the Fimbrin and the Total Outer Membrane Protein

The outer membranes proteins were isolated according to a modified procedure based on Carlone et al., "Rapid microprocedure for isolating detergent-insoluble outer membrane proteins from Haemophilus species." (1986), J. Clin. Microbiol. 24:330. NTHi strain 1885 and strain 1128 were each cultured as follows. The NTHi were grown for 18 hours in Brain Heart Infusion Broth containing: 2 mg. NAD/1; 2 mg. hemin/1 and incubated at 37 C. in a humidified atmosphere of 5% $CO_2$ and 95% air. Then the NTHi were collected by centrifugation at 4000 x g for 20 minutes at 4° C., and decanted. The NTHi pellets were resuspended in 10 mM HEPES buffer, pH 7.4, and sonicated for three 20 second pulses on ice using an Artek Sonic Dismembrator, Model 150 from Artek Systems Corp. at a setting of 60%. The sonicates were centrifuged at 9100 x g for 5 minutes at 4° C. The pellets were collected and the supernatant was centrifuged again to recover the crude outer membrane fraction. The pellets were combined and resuspended in 10 mM HEPES buffer and mixed in equal volumes with 2% sarcosyl (w/v) in the 10 mm HEPES buffer. The suspensions were incubated at room temperature for 60 minutes with occasional shaking. The suspension was then centrifuged at 5900 x g for 30 minutes at 4° C. and the pellet was collected. The pellets were gently surface-washed with 200 ml double distilled water without resuspending the pellets. The pellets were individually resuspended in 20 ml double distilled water to provide a outer membrane protein suspension. The outer membrane protein suspension was then aliquoted, frozen and maintained at 70° C. The total outer membrane protein isolated in the above described manner, from NTHi strain 1128 was then used as an immunogen for active immunization of animals.

To isolate the fimbrin protein, aliquots of the total outer membrane suspension were applied to large, 5–20% continuous gradient polyacrylamide gels known in the art as "slab" gels. The slab gels were run at 30 mA/gel for approximately 4 hours and rinsed in water. The slab gels were negatively stained with a reversible protein stain (ISS PRO-GREEN™ staining system, available from Integrated Separation Systems according to the manufacturer's instructions for 10 minutes or overnight). The fimbrin band was identified via its migration relative to molecular mass standards run in adjacent lanes. The 25.5 kD band was excised from the gel using a razor blade, to obtain the fimbrin protein, although the 37.5 kD band may also be used, if the 37.5 kD fimbrin protein can be reassembled to its secondary structure. The 37.5 kD band contains the fully denatured form of the fimbrin protein. To obtain the fimbrin protein, the entire 25.5 kD bands were excised and cut into pieces approximately 1 cm. in length. The bands were destained according to the instructions provided by Integrated Separation Systems. Next, four to six gel pieces were placed in electroelution tubes and subjected to electroelution for 4 hours at 9 mA/tube. The electroeluted protein was collected in the reservoir tip of the electroelution tube from Bio-Rad Electro-Eluter and membrane caps w/12,000 MWCO. The electroeluted protein were dialyzed against distilled water for about 24 hours using 10,000 molecular weight cut off dialysis membrane available from Spectrum Micro-ProDiCon Houston, Tex. The above procedures were repeated, usually twice, until silver staining of electrophoresed SDS-PAGE preparation indicated a lack of contamination with other outer membrane proteins. The fimbrin protein isolated in the above described manner, from NTHi strain 1128 and 1885 was also used as an immunogen for the active immunization of animals.

The outer membrane protein preparations were additionally observed via transmission electron microscopy of negatively stained preparations to confirm the reassembly of the isolated fimbrial protein into filaments upon dialysis.

Active Immunization

Five cohorts of 10 chinchillas each were actively immunized with either a saline control preparation or one of the following immunogens: a total outer membrane protein preparation from strain #1128; isolated fimbrin protein from NTHi strain #1128; isolated fimbrin protein from NTHi strain #1885; or an isolated major outer membrane protein approximately 40.5 kDa which constitutes the predominate outer membrane protein of strain #1128 but which is unrelated to the fimbrin subunit. The 40.5 kD major outer membrane is also known in the art as the "P2" protein. All immunogens were assessed for endotoxin content prior to their use as an immunogen via a chromogenic Amoebocyte Lysate assay which is commercially available from Whittaker Bioproducts under the designation QCL-1000. The chinchillas were subcutaneously injected with 100 µg immunogen in complete Freund's adjuvant. Then 30 days layer they received 50 µg of the same immunogen in incomplete Freund's adjuvant. Following the second immunization, these five cohorts were divided into two groups each and challenged transbullarly with either strain #1128 or #1885. The chinchillas were assessed over a 4-week period for: tympanic membrane pathology by otoscopic examination; semiquantitation of NTHi recovered via epitympanic tap of the inferior bulla; and light microscopic examination of fixed middle ear mucosal epithelium and tympanic membrane for histopathology.

As shown in Tables 3 and 4, the total outer membrane protein preparation and isolated fimbrin protein from strain #1128 were equally effective in significantly reducing tympanic membrane pathology ($p \leq 0.001$) for chinchillas challenged with the homologous fimbriated NTHi strain that is with NTHi strain 1128. Immunization with total outer membrane protein from strain 1128 also protected against the heterologous challenge with NTHi strain 1885 ($p \leq 0.001$) and was more likely to render middle ears effusion-free or culture-negative than immunization with the fimbrin protein. Immunization with fimbrin protein derived from strain 1885 was somewhat less protective against both homologous challenge ($p \leq 0.01$) and heterologous challenge ($p \leq 0.02$). Immunization with the major outer membrane protein, weighing approximately 40.5 kDa, did not protect against challenge with either strain 1128 or 1885. Indeed chinchillas receiving the approximately 40.5 kDa major outer membrane protein demonstrated significantly worse tympanic membrane pathology upon otoscopy ($p \leq 0.005$).

Figure 2:
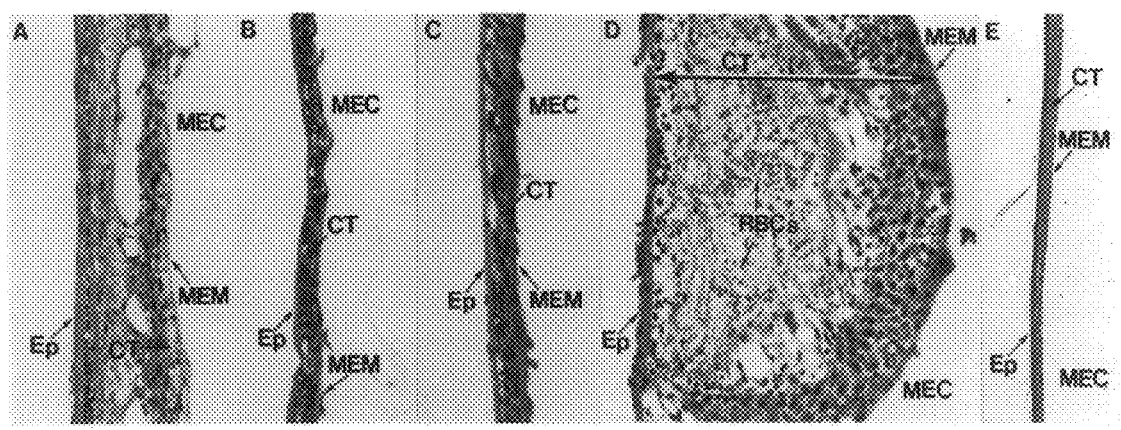
FIG. 2 is a collection of light micrographs of H&E stained tissue sections of tympanic membrane from immunized chinchillas which received the homologous NTHi strain #1128. Chinchillas were immunized with: (A) control preparation; (B) total outer membrane protein #1128; (C) isolated fimbrin protein #1128; (D) isolated major outer membrane protein #1128. Micrograph (E) shows normal chinchilla tympanic membrane. All micrographs are at a magnification of 210 x. The following designations are used to identify the following tissues: Ep—epidermal layer; CT—connective tissue of fibrous layer; MEM—middle ear mucosa; MEC—middle ear cavity; and RBCs—erythrocytes. Tympanic membrane (TM) of control chinchilla (A) demonstrates thickened and edematous CT layer. Note minimal thickening of tympanic membrane relative to normal (E) in B and C. Chinchillas immunized with the isolated major outer membrane protein of strain #1128 (D) demonstrate marked thickening of the tympanic membrane with bleeding evidenced by the presence of red blood cells connective tissue in the (RBCs) and edema in the fibrous layer (CT).

The chinchillas immunized with the control saline preparation demonstrated moderate histopathology of both tympanic membranes and middle ear mucosa. As shown in FIG. 2, tympanic membranes were thickened with an edematous fibrous layer, whereas middle ear mucosa specimens dem onstrated minimal thickening of the mucosa, osteoneogenesis and the presence of both red blood cells and inflammatory cells in the subepithelial space. A dense polymorphonuclear leukocytic exudate was present in the middle ear cavity.

Figure 3:
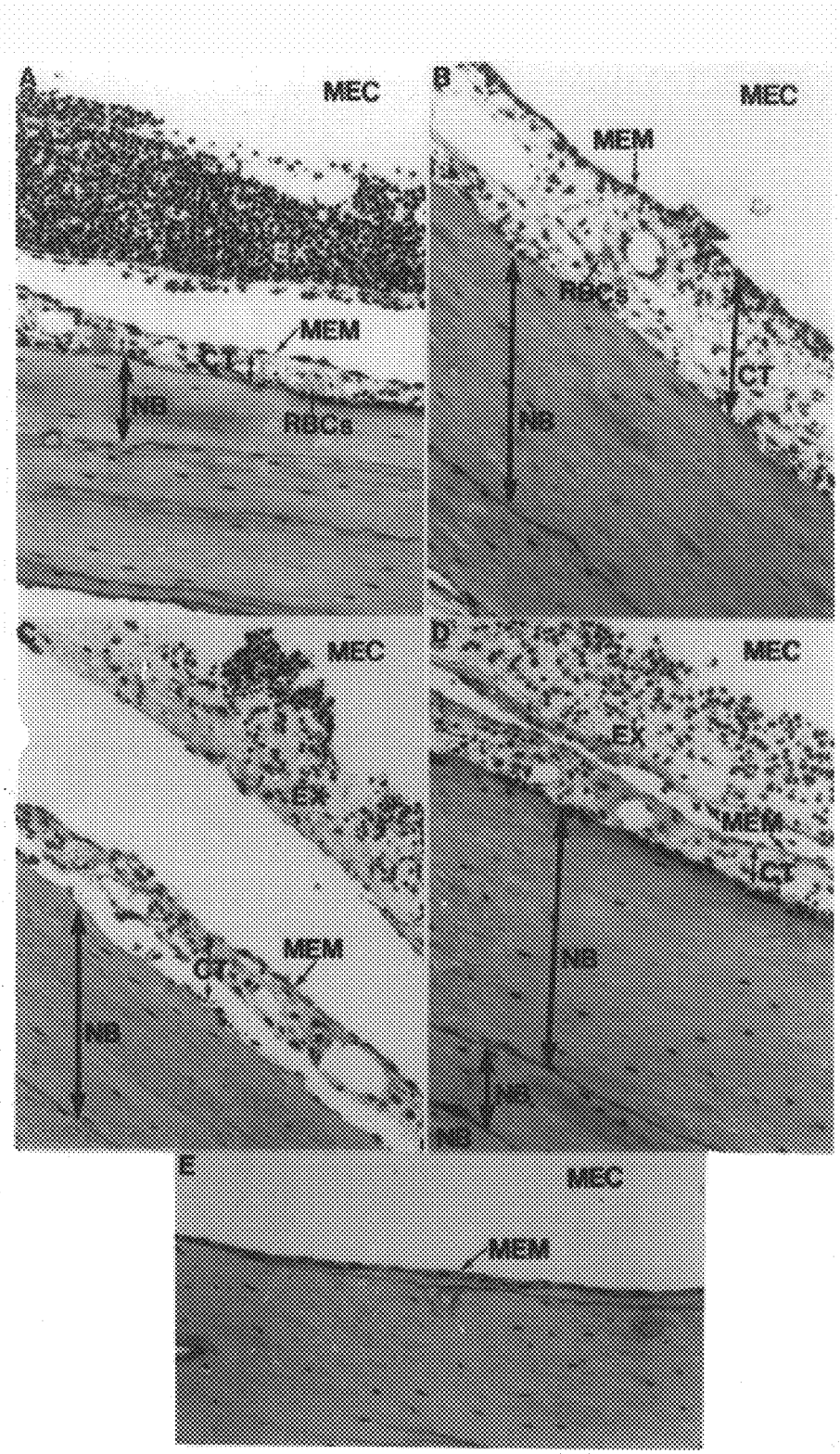
FIG. 3 is a collection of light micrographs of H&E stained tissue sections of middle ear mucosa from immunized chinchillas which received the homologous NTHi strain #1128. Chinchillas were immunized with (A) control preparation; (B) total OMP #1128; (C) isolated fimbrin protein from NTHi 1128; (D) major outer member protein isolated from strain #1128. Micrograph (E) is that of normal chinchillas middle ear mucosa. All micrographs are at a magnification of 210 x. EX—exudate; MEC—middle ear cavity; MEM—middle ear mucosa; NB—new bone (osteoneogenesis); RBCs—erythrocytes; CT—connective tissue.

Chinchillas immunized with either total outer membrane protein, or fimbrin protein isolated from NTHi strain 1128 demonstrated reduced tympanic membrane histopathology compared to the control chinchillas. The administration of total outer membrane protein, rather than fimbrin protein, more often resulted in effusion-free ears or sterile effusions. As shown in FIG. 3, the administration of total outer membrane protein resulted in an absence of a polymorphonuclear leukocytic comprised exudate overlying the middle ear cavity. FIG. 3 reveals minimal thickening of mucosal layer in control chinchillas (A) relative to normal (E). There is a dense polymorphonuclear leukocytic exudate present in the middle ear cavity which is typically seen post-induction of otitis medua with NTHi. Chinchillas immunized with total outer membrane protein (B) demonstrate significant thickening of the CT layer of the mucosa with bleeding into the subepithelial space as evidenced by the presence of red blood cells and some new bone formation. Chinchillas immunized with fimbrin protein (C) are similar to those immunized with total outer membrane protein (B) but with the addition of a predominantly polymorphonuclear leukocyte comprised exudate in the middle ear cavity. Chinchillas immunized with the isolated major outer membrane protein of strain 1128 (D) demonstrated similarly inflamed middle ear mucosa (as did all NTHi-challenged chinchillas) with the additional of extensive osteoneogenesis, a more predominant mononuclear character to the exudate and evidence of focal desquamation of the epithelial layer of the middle ear membrane, the severity of which was not seen in other cohorts.

Thus antibodies induced by vaccination with fimbrin or outer membrane protein and directed against fimbrin protein contribute to protection against NTHi-induced otitis media.

Figure 8:
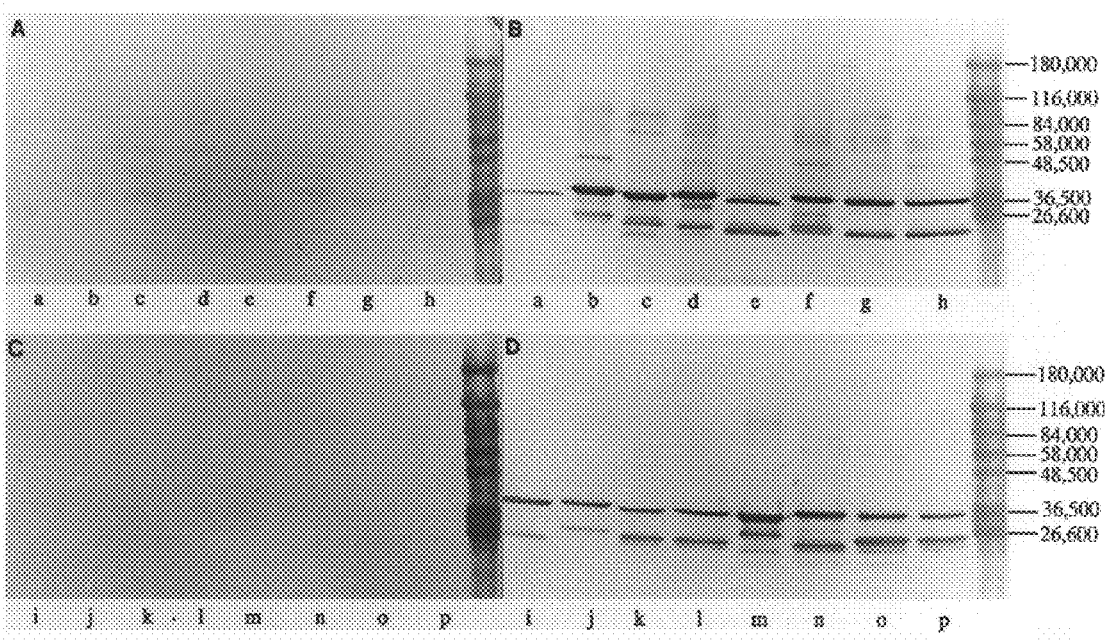
FIG. 8 shows a western blot analysis of: normal chinchilla serum pool in A & C serum obtained post-immunization with which isolated fimbrin protein from strain #1128 in B & D versus total outer membrane protein preparations from *Haemophilus influenzae* clinical isolates (non-typable and type b): (a) 86-042; (b); 86-043; (c) 1667 MEE; (d) 1128; (e) 1885 MEE; (f) 169 p+; (g) 90-100 L; (h); 90-100 R; (i) 90-111 L; (j) 90-112 R; (k) 90-114 NP; (l) 90-114 L; (m) Mr 13 p−; (n) Mr 13 p+; (o) Eagan p+; (p) Egan p−.

Since the fimbrin protein, whether isolated from NTHi or present as a component in a total outer membrane protein preparation, provides protection against otitis media by active and passive immunization, it is suitable for use immunization agent. In order to afford the broadest range of protection, a vaccinogen should elicit an immune response that is both protective and broadly cross-reactive. Since there is considerable heterogeneity among otitis media isolates of NTHi, total outer membrane proteins were isolated from the bacterial outer membranes of 15 randomly selected type b and non-typable clinical isolates of *Haemophilus influenzae*. To determine the extent of protection and cross reactivity of the vaccine, the bacterial outer membranes were solubilized in detergent and subjected to a Western blot of SDS-PAGE with polyclonal chinchilla antiserum directed against the isolated fimbrin protein from NTHi strain 1128. As shown in FIG. 8, the Western blot showed that the polyclonal chinchilla antiserum recognized similarly migrating bands in all 15 of the bacterial outer membrane isolates indicating that the fimbrin protein in each of the 15 strains are serologically related. Therefore, the fimbrin proteins from the 15 different strains share common epitopes. Thus, fimbrin isolated from NTHi 1128 strain is a particularly suitable immunogen to protect against the different non-typable *H. influenzae* that cause otitis media.

TABLE 3

Active Immunization Trial
Average Tympanic Membrane Pathology (n = 5 ears)

| Immunogen | Challenge NTHi Strain | Days Post-Intrabullar Challenge | | | | | | | | | | | | | |
|---|---|---|---|---|---|---|---|---|---|---|---|---|---|---|---|
| | | 1* | 2 | 3* | 4 | 7* | 8 | 9 | 10* | 11 | 14* | 15 | 16 | 17* | 18 | 28 |
| Control | 1128 | 2+ | 2+ | 2+ | 3+ | 2+ | 3+ | 3+ | 3+ | 3+ | 3+ | 2+ | 2+ | 2+ | 3+ | 2+ |
| | 1885 | 1+ | 1+ | 2+ | 1+ | 2+ | 2+ | 2+ | 2+ | 1+ | 2+ | 2+ | 1+ | 2+ | 1+ | 1+ |
| NTHi #1128 total OMP | 1128 | 1+ | 2+ | 2+ | 2+ | 2+ | 2+ | 2+ | 2+ | 2+ | 1+ | 1+ | 1+ | 1+ | 1+ | 1+ |
| | 1885 | 1+ | 2+ | 2+ | 1+ | 1+ | 1+ | 1+ | 1+ | 1+ | 1+ | 1+ | 1+ | 0 | 0 | 0 |
| NTHi #1128 major OMP | 1128 | 2+ | 3+ | 4+ | 3+ | 3+ | 3+ | 3+ | 3+ | 3+ | 3+ | 3+ | 3+ | 3+ | 3+ | 3+ |
| | 1885 | 1+ | 2+ | 3+ | 2+ | 3+ | 3+ | 3+ | 3+ | 3+ | 3+ | 3+ | 2+ | 2+ | 2+ | 2+ |
| NTHi #1128 fimbrial protein | 1128 | 2+ | 2+ | 1+ | 2+ | 2+ | 1+ | 1+ | 1+ | 1+ | 1+ | 1+ | 2+ | 1+ | 1+ | 0 |
| | 1885 | 1+ | 2+ | 2+ | 2+ | 2+ | 2+ | 2+ | 2+ | 2+ | 2+ | 2+ | 2+ | 2+ | 2+ | 1+ |
| NTHi #1885 fimbrial protein | 1128 | 2+ | 3+ | 3+ | 3+ | 3+ | 3+ | 4+ | 3+ | 3+ | 3+ | 3+ | 3+ | 2+ | 2+ | 1+ |
| | 1885 | 1+ | 1+ | 1+ | 1+ | 1+ | 1+ | 1+ | 1+ | 1+ | 1+ | 1+ | 1+ | 1+ | 1+ | 0 |

Challenge dose: 2.5–3.5 E 3 c.f.u.
*Denotes day of epitympanic tap
OMP — outer membrane protein

TABLE 4

Active Immunization Trial
Statistical Comparison by Group

| Immunogen | NTHi Challenge Strain | p-value | Status Relative to control |
|---|---|---|---|
| Control | | ND | |
| 1128 total OMP | | p ≦ 0.001 | + |
| 1128 major OMP | 1128 | p ≦ 0.005 | − |
| 1128 fimb. prot. | | p ≦ 0.001 | + |
| 1885 fimb. prot. | | p ≦ 0.002 | NS |
| Control | | ND | |
| 1128 total OMP | | p ≦ 0.001 | + |
| 1128 major OMP | 1885 | p ≦ 0.001 | − |
| 1128 fimb. prot. | | p ≦ 0.13 | NS |
| 1885 fimb. prot. | | p ≦ 0.01 | + |

+ indicates less tympanic membrane pathology relative to control
− indicates greater tympanic membrane pathology relative to control
"p" indicates probability

Cloning and Sequencing of the Fimbrin Gene

Chromosomal DNA isolated from NTHi strain 1128 was sheared by sonication and DNA fragments ranging from 2 to 5 kb were isolated using a 1% agrose gel. The fragments were attached to the Not-EcoRI linker-adapters from Stratagene Co and ligated with λgt11 arms from Stratagene Co. The ligated DNA was packaged in vitro into lambda particles by using Gigapack Plus from Stratagene according to the manufacturer's instructions, to provide a genomic library. To screen the genomic library by plaque hybridization, a 624 base pair polymerase chain reaction product probe was prepared as described below.

First the fimbrin protein from strain 1128 isolated as described above was digested with CNBr by suspending 500 ug fimbrin protein in 100 ul of 70% formic acid with 500 ug CNBr in 70% formic acid and 5 ug tryptophan. The digested protein was recovered and rinsed several times with distilled water.

The digested protein fragments were applied to a polyacrylamide gel then run at the same conditions as described above, then transferred to an Imobilon membrane from Millipore Co. All bands containing above about 2 picograms were excised, then the protein fragments were commercially sequenced by University of Southern California, at Riverside, using an applied Biosystems 475 A pulsed liquid protein sequencer and Applied Biosystems Computing Integrator. The two most prodominant bands containing the protein fragments produced the N-terminus and an internal peptide which yielded the following two sequences of 20 and 15 amino acids respectively:

APQENTFYAGVKAGQGSFHD (SEQ. ID. NO. 3) and VSKTFSLNSDVTFAF (SEQ. ID. NO. 4). Based on these amino acid sequences, two nucleotide sequences were synthesized using Applied Biosystems Synthesizer and purified through oligonucleotide cartridges from Applied Biosystems. The two nucleotide sequences were: a 20-mer oligonucleotide with 128-fold degeneracy corresponding to Gln3 through Ala9: 5'CA(AG)GA(AG)AA (CI)AC(AGTC) TT(CI)TA(CT)GC 3' (SEQ. ID. NO. 5) and a 18-mer oligonucleotide with 512-fold degeneracy corresponding to the Phe 15 through Asp10: 5' AAA (AGTC)GC(AG)A(AGTC)GT(AGTC)AC(GA)TC 3' (SEQ. ID. NO. 6). The 18-mer oligonucleotide was used as a sense primer and the 20-mer-oligonucleotide was used as an antisense primer to amplify the genomic DNA fragment encoding the N-terminal region of the fimbrin protein. The polymerase chain reaction product was obtained by preparing a mixture containing combining 100 ng gemonic DNA, 50 pmol of the 20-mer oligonucleotide primer, 50 pmol of the 18-mer oligonucleotide primer, 10 nmol of each deoxynucleoside triphosphate, and 5 units Taq DNA polymerase from GibcO-BRL in a final volume of 100 μl. The genomic DNA in the mixture was denatured at 94° C. for about 1 minute, then annealed at 50° C. for about 2 minutes, and extended at 72° C. for about 2 minutes. A last elongation step was done at 72° C. for about 10 minutes, to provide a mixture containing the polymerase chain reaction amplified product. The polymerase chain reaction amplified product was run on an agarose gel, then purified from the agarose gel and labeled with $^{32}$P using the random labeling kit from Boehringer Mannheim Co. to provide a radio labeled 624 base pair polymerase chain reaction product probe.

The genomic library was screened by using the 624 base pair polymerase chain reaction product as a hybridization probe according to Sambrook, Fritsch and Mantiatis (1989) "Molecular Cloning a Laboratory Manual" 2nd ed., Cold Spring Harbor Laboratory, Cold Spring Harbor, N.Y. The 624 base pair polymerase chain reaction product hybridized with 3 phage plaques from the genomic library. The hybridization was carried out overnight at 42° C. with standard solutions as disclosed in Sambrook, Fritsch and Mantiatis (1989) "Molecular Cloning a Laboratory Manual" 2nd ed., Cold Spring Harbor Laboratory, Cold Spring Harbor, N.Y., containing 50% formamide, then filtered. The filters were washed for 30 minutes at 65° C. in 0.1% XSSC and 11% SDS, then exposed to x-ray film. The positive plaques were identified from the radiograms and recovered from agar plugs. The three DNA fragments from the phage plaques were designated clones "λFD 1", "λFD 2", and "λFD 3". The phage DNA was isolated, digested with ECoRi, isolated by spin elution. The DNA fragments were then subcloned into plasmid pUC18 which is available from Sigma. The *Haemophilus influenzae* DNA fragments inserted into these phages created plasmids designated "FD1", "FD2" and "FD3". Sequencing of these plasmids revealed that they encoded different overlapping portions of the fimbrin gene sequence but none of them contained the full length gene. Plasmids FD1 and FD3, which contain an overlap of 237 base pairs were used to construct a plasmid carrying the complete coding sequence as well as 5' and 3' flanking regions of the fimbrin gene. The EcoRI-HindIII fragment of plasma FD1, containing the 5' upstream region and the first 450 base pairs of the fimbrin gene was isolated and inserted in the EcoRI-HindIII digested and dephosphorylated plasma FD3 to create a plasmid designated "FD".

Figure 1:
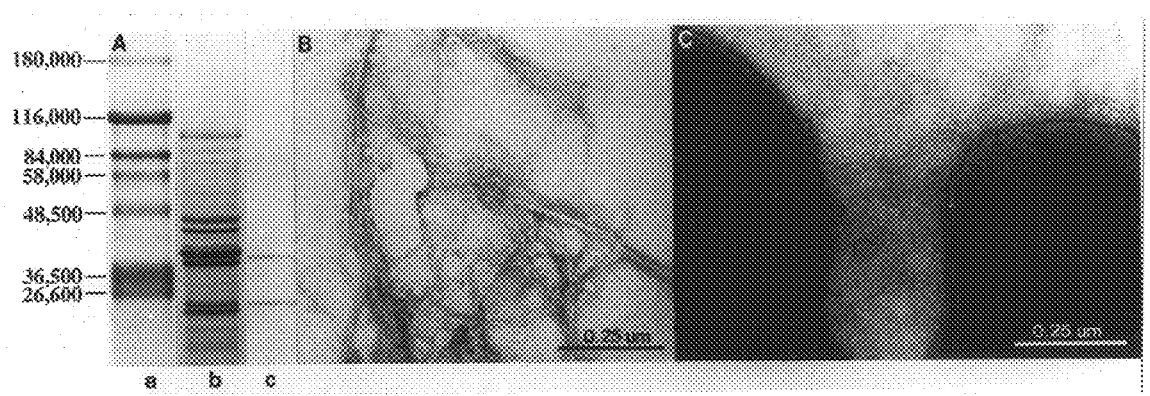
FIG. 1 is an A) Coomassie brilliant blue stained sodium dodecylsulfate-polyacrylamide gel electro phoretigram (SDS-PAGE) of: (a) molecular weight standards; (b) total outer membrane protein preparation from NTHi strain #1128 and (c) isolated fimbrin protein from strain #1128.

The nucleotide sequence of the fimbrin gene was determined from the insert fragment in plasmid λFD. Both strands of this insert were sequenced by the Sanger dideoxy-mediated chain terminated method, according to Sambrook, Fritsch and Mantiatis (1989) "Molecular Cloning a Laboratory Manual" 2nd ed., Cold Spring Harbor Laboratory, Cold Spring Harbor, N.Y., using the commercially available sequencer Sequence 2.0 from U.S. Biochemical Co. The DNA sequence and the deduced amino acid sequence are shown in FIG. 5. The entire fimbrin gene contained a 1077 base pair Open reading frame, beginning with an ATG codon at position 406 and ending with a TAA stop codon at position 1085. The Open reading frame is preceded by a putative ribosome-binding site AGGA similar to the consensur sequence for *E. coli* and beginning eleven base pairs upstream of the initiation codon. One stem-loop structure consistent with a rho-independent transcription terminator is located downstream of the open reading frame. Preceding the coding sequence for the mature fimbrin protein was encoded a leader peptide of 21 amino acid residues with the characteristics of a typical signal sequence. The fimbrin gene is first translated as a precursor form consisting of 359 amino acids (SEQ. ID. NO. 2) and later the signal sequence is processed to yield the mature fimbrin protein consisting of 338 amino acids. The calculated molecular mass is 36.4 kDa, which is almost identical to the molecular mass of the upper band in the SDS-PAGE, shown in lane 3 of FIG. 1A. This band is believed to be the true fimbrin protein. The deduced amino acid sequence for the fimbrin gene agreed with the amino acid sequences of the N-terminus and an internal peptide derived from CNBr cleavage of the purified fimbrin protein, shown in FIG. 5.

The open reading frame coding for fimbrin protein described herein can be used to express the recombinant protein in *E. coli* or other expression systems. Two examples are described below.

EXAMPLE 1

Figure 9:
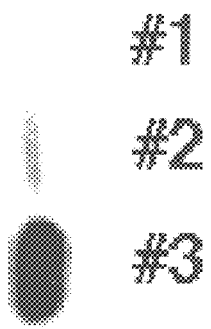
FIG. 9 is a western blot analysis of cell lysates prepared from *E. coli* BL21 (DE3)/pLys S transformed with pET3a (lane 1) and pNHF before (lane 2) and after (lane 3) induction with 0.5 mM IPTG. The blot was probed with polyclonal chinchilla serum directed against the isolated fimbrin protein from NTHi strain #1128 diluted 1:250.

Two oligonucleotides based on the first six codons and the last six codons of the coding sequence of the fimbrin gene served as primers in a polymerase chain reaction to amplify the coding sequence of the fimbrin gene employing genomic DNA from NTHi #1128 as a template. The synthesized polymerase chain reaction product was double digested for 1 hour at 37° C. with BamHI and NdeI and subcloned in the corresponding cloning sites of the expression vector pET3a from New England Biolabs according to Alan H. Rosenberg, et al., Gene, 1987, 56:125, and ligated overnight at 14° C., using T4 ligase, to yield plasmid pNHF. The ligated DNA was transformed into *E. coli* DH5α and the desired construction was verified by restriction analysis with BamH1 and Nde1. The vector pET3a and plasmid pNHF were transformed into *E. coli* BL21(DE3)/pLysS. Expression of the fimbrin gene product under the control of the φ10 promoter was achieved by induction of T7 RNA polymerase synthesis by the addition of 0.5 mmole IPTG. The whole cell protein profile of BL21(DE3)/pLysS[pNHDF] was analyzed and compared to the profile of BL21(DE3)/pLysS[pET3a]. Western blot analysis shown in FIG. 9 showed that *E. coli* expressed the recombinant protein.

EXAMPLE 2

Figure 10:
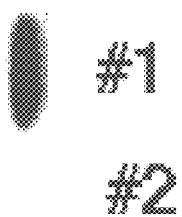
FIG. 10 shows the expression of fimbrin protein in recombinant (lane 1) and wild type (lane 2) baculovirus-infected cells. The infected cell extracts were analyzed by SDS-PAGE and western blotting with polyclonal chinchilla serum directed against the isolated fimbrin protein from NTHi strain #1128 (1:250 dilution) as the primary antibody.

Fimbrin protein can also be expressed using baculovirus vector according to Luckow, V. A., Recombinant DNA technology and Applications, eds., Prokop, A. Bajpai, R. K. and Ho, C. S. (McGraw, Inc., N.Y.) 1991, 1097, in insect cells. A recombinant pBacPAK transfer vector was constructed by cloning the polymerase chain reaction-amplified coding sequence of the fimbrin gene into the BamHI site of pBacPAK1 vector from Clontech Laboratories, Inc. Palo Alto, Calif. following the manufacturer's instructions. After screening for the correct orientation of the insert using Hind III digestion, the recombinant gene was incorporated into the viral genome by cotransfecting insect cells, *Sporodoptera frugiperda,* with a mixture of wild type viral DNA and transfer vector DNA. Individual plaques were obtained and the recombinant viruses were tested for expression of fimbrin protein. Western blot analysis shown in FIG. 10, indicates that the insect cells expressed *H. influenzae* fimbrin protein.

The fimbrin protein expressed may be used as a vaccine to prevent and/or reduce the severity, to study, and to treat otitis media in animals.

Insertional Mutagenesis of the Fimbrin Gene

Figure 6:
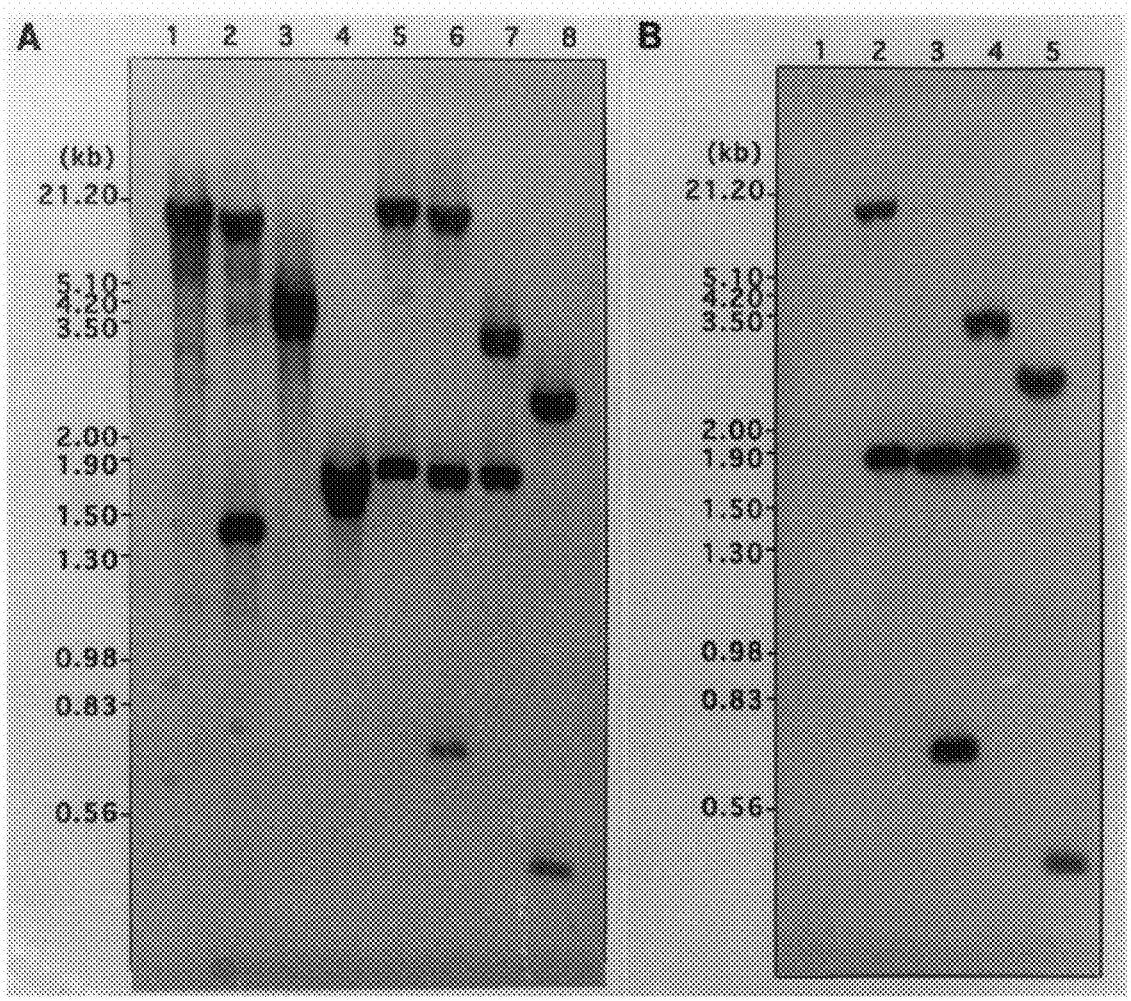
FIG. 6 is a southern hybridization blot/analysis. Genomic DNA from NTHi #1128 parent strain were run in panel A, lanes 1, 2, 3, 4 and panel B, lane 1 and the DNA from the mutant strain were run in panel A, lanes 5, 6, 7, 8 and panel B, lanes 2, 3, 4, 5. DNA that was digested to completion with EcoRI was run in panel A, lanes 1 and 5 and panel B, lanes 1 and 2; EcoRI-HindlII (Panel A—lanes 2, 6 and Panel B—lane 3), EcoRI-PstI (Panel A—lanes 3, 7 and Panel B—lane 4) and TaqI (Panel A—lanes 4, 8 and Panel B—lane 5), electrophoresed on a 1% agarose gel, transferred to nitrocellulose membrane and probed with $^{32}$P-labeled fimbrin gene (Panel A) and $^{32}$P-labeled chloramphenicol acetyltransferase gene (Panel B).
Figure 7:
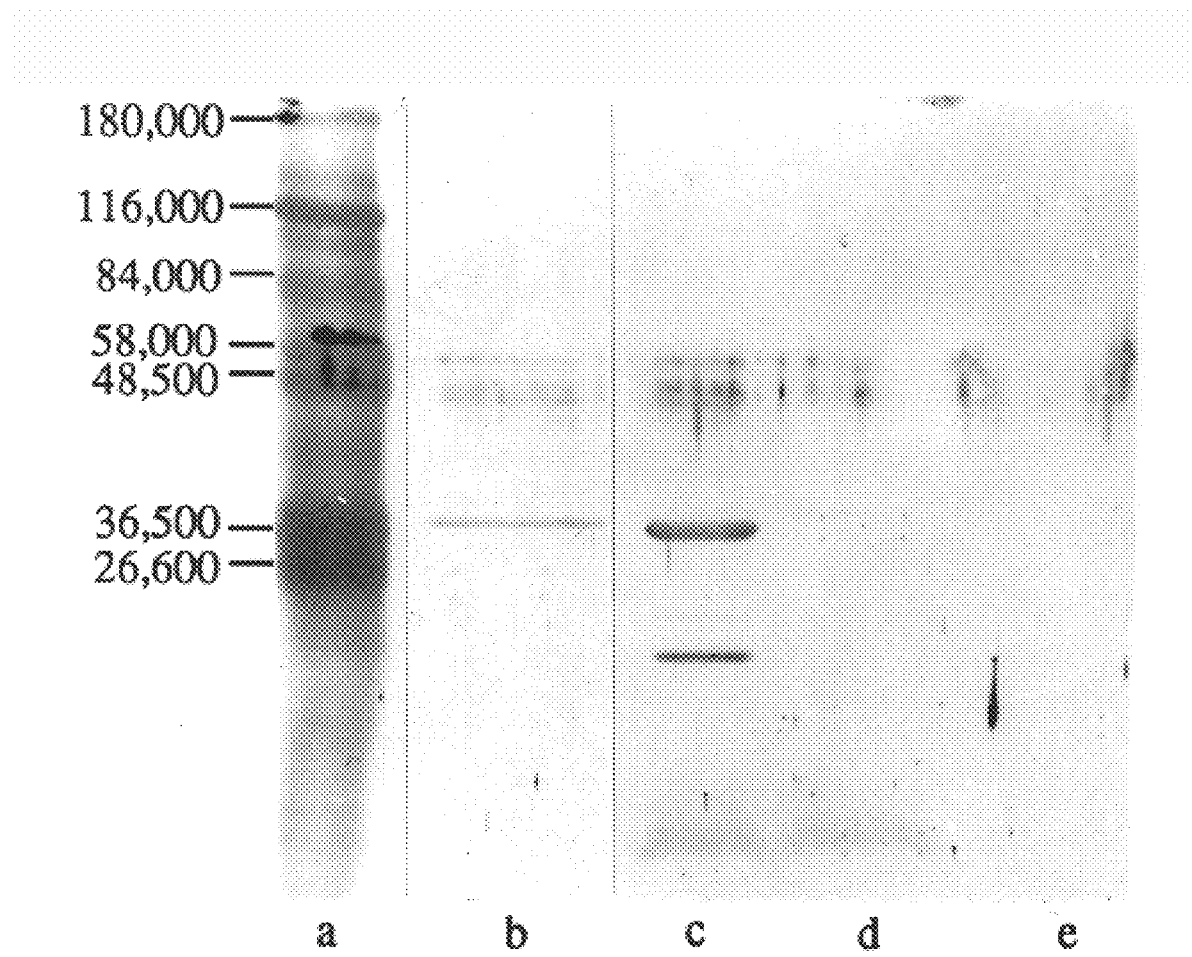
FIG. 7 Western blot with chinchilla polyclonal antiserum directed against the upper band of the isolated fimbrin protein of the parental NTHi strain #1128 versus: (b) NTHi strain #1128 isolated fimbrin protein (upper band); (c) NTHi strain #1128 total outer membrane protein; (d) mutant strain total outer membrane portion; (e) mutant strain isolated lower band. Lane (a) contains prestrained molecular weight standards.

As shown in FIG. 6, the results of genomic Southern hybridization analysis of DNA from NTHi #1128 cleaved with a variety of restriction enzymes indicates that only a single copy of the fimbrin gene is present in strain #1128. The 952 base pair SfuI fragment from pBR325, containing the gene encoding chloramphenicol acetyl-transferase was blunt ended using 8 K gm phosphatase, from Epicenter Technologies, Madison Wis., and ligated with T4 ligase to the Bst EII digested plasmid FD dephosphorylated and filled with Klenow enzyme in the presence of the four deoxy-nucleoside triphosphates. This plasmid was transformed into competent *E. coli* DH5α and the transformants were selected on LB agar containing 100 λlg/ml ampicillin and 25

λlg/ml chloramphenicol. One recombinant was designated "NFM". Restriction enzyme mapping of this NFM strain verified the position of the chloramphenicol cassette and verified that a single copy of the gene was inserted. The pNFM plasmid was purified, linearized with BamHI and transformed into NTHi #1128, made competent by the M-IV method according to Herriot et al. "J. Bacteriology" (1970) vol. 101 pp. 517–524, which is incorporated herein by reference. Mutants were selected on supplemented brain heart infusion agar containing 2 λlg/ml chloramphenicol. Genomic DNA isolated from one of these mutants and from the parent, 1128 was digested with EcoRI, EcoRI HindIII, EcoRI PstI and Taq I and analyzed by Southern hybridization. EcoRI and Taq I cleave once inside the chloramphenicol gene and HindIII cuts once within the fimbrin gene downstream the point of insertion of the chloramphenicol cassette. The 952 base pair SfuI fragment from pBR325 encoding the chloramphenicol gene and the 1077 base pair EcoRI-BamHI fragment encoding the fimbrin gene, were used as $^{32}$P-labeled hybridization probes. The autoradiograms are shown in FIG. 6. The mutant strain was compared with the parent strain #1128 by western blot analysis with the polyclonal antifimbrial chinchilla serum prepared against the upper band to detect immunoreactive proteins from whole cell extracts. This cross-reactive band was absent in the mutant, as shown in FIG. 7. Coomassie staining indicated two fimbrin protein bands, one at about 37.5 kDa and another at about 25.5 kDa corresponding to the bands in FIG. 1.

This lower band from the fimbrin gene-disrupted mutant strain did not cross react with the antibodies prepared against the 37.5 kD fimbrin protein. Variable degrees of cross reactivity with the 25.5 kD band were seen with the parent. These results suggest that the protein in the lower band can associate with the 37.5 kD fimbrin protein. To determine whether the lower band found in the mutant is involved in fimbriae formation, the lower band from the parent strain and the mutant strain, were examined electron microscopically with and without the addition of the 36 kDa protein. Only the parent strain showed fimbriae and, therefore, the lower band seen in the mutant is unrelated to fimbriae.

Effect of Fimbrin Gene Disruption on Fimbrae

While negative staining and immunogold labeling revealed a fimbrae on the parent strain, no surface appendages were found on the mutant strain. The mutant strain was found to be 32–36% less adherent than the parent strain to eukaryotic target cells.

The pathogenicity of the parent strain and the mutant strain were compared. Ten chinchillas were inoculated with the NTHi; 5 chinchillas received the parent strain and 5 received the mutant strain. Dosage received was: 3.3 E 3 cells of the parent strain and 4.0 E 3 cells mutant strain. The NTHi was inoculated into the left superior bulla of the chinchilla, and sterile saline was inoculated into the right superior bullae as a control. The results are shown in Table 5. While differences in tympanic membrane pathology over time were not remarkable, survival rates were notably different between the two strains. Labyrinthine involvement, that is the effect of the inner ear, manifested by balance disorder was noted in all of the chinchillas receiving the parent strain. In comparison, 3 of the chinchillas receiving the mutant strain developed mild to moderate labyrinthine involvement.

TABLE 5

Semi-quantitative Assessment of Viable Bacteria in Epitympanic Tap Fluids Post-Transbullar Challenge with NTHi strain #1128 and Mutant #1

| | | CFU/ml | |
| --- | --- | --- | --- |
| Animal # | Strain Received | Choc. agar | BHI |
| 1 | Parent | >10$^8$ | >10$^8$ |
| 2 | Parent | >10$^8$ | >10$^8$ |
| 3 | Parent | 2.1 E 7 | 6.7 E 6 |
| 4 | Parent | >10$^8$ | 2.0 E 7 |
| 5 | Parent | Dry | Dry |
| 6 | Mutant | Dry | Dry |
| 7 | Mutant | Dry | Dry |
| 8 | Mutant | 2.9 E 6 | 4.8 E 4 |
| 9 | Mutant | 6.9 E 5 | 4.1 E 4 |
| 10 | Mutant | 1.4 E 5 | 2.5 E 4 |

*Tap performed 4 days post-inoculation of left middle ear of all chinchillas.

In an intranasal challenge study, 12 chinchillas were inoculated via passive inhalation of approximately 10$^8$ cfu of either the parent strain or mutant strain. Assessment of tympanic membrane pathology, shown in Table 7, indicated significantly reduced pathology in chinchillas inoculated with the mutant strain. Labyrinthine involvement was markedly reduced in chinchillas receiving the mutant strain. By day 13 there were only 3 chinchillas left alive in the parent cohort compared to 6 in the mutant cohort.

Thus, the ability of the mutant strain to gain access to, survive and multiply in the middle ear cleft was significantly hampered.

TABLE 6

Labyrinthine Involvement in Chinchillas Receiving A Transbuller or Intranasal Inoculation of NTHi strain #1128 or Mutant #1

| Post trans-buller Inoc. | Severity of Disease | | | | | | | |
| --- | --- | --- | --- | --- | --- | --- | --- | --- |
| | None | Mild | Moder. | Severe | None | Mild | Moder. | Severe |
| Day 3 | * | — | — | — | * | — | — | — |
| Day 4 | ⊗ | — | ⊙ | ⊙ | * | — | — | — |
| Day 5 | ⊙ | — | ⊙ | ⊗ | ⊗ | ⊙ | — | — |
| Day 6 | ⊙ | — | ⊙ | ⊗ | ⊗ | — | ⊙ | — |
| Day 7 | ⊙ | — | — | ⊗ | ⊗ | ⊙ | — | — |
| Day 8 | ⊙ | — | ⊙ | ⊙ | ⊗ | ⊙ | — | — |

TABLE 6-continued

Labyrinthine Involvement in Chinchillas Receiving A
Transbuller or Intranasal Inoculation of NTHi strain
1128 or Mutant #1

| Post trans-buller Inoc. | Severity of Disease | | | | | | | |
|---|---|---|---|---|---|---|---|---|
| | None | Mild | Moder. | Severe | None | Mild | Moder. | Severe |
| Day 9  | ⊙ | — | — | ⊗ | ⊗ | ⊙ | — | — |
| Day 10 | ⊙ | — | — | ⊗ | ⊗ | ⊙ | ⊙ | — |
| Day 11 | ⊙ | — | — | ⊗ | ⊗ | ⊙ | — | ⊙ |
| Day 12 | ⊙ | — | — | ⊗ | ⊗ | — | ⊙ | ⊙ |
| Day 13 | ⊙ | — | ⊙ | ⊙ | ⊗ | — | ⊙ | ⊙ |
| Day 3  | * | — | — | — | * | — | — | — |
| Day 4  | ⊗ | — | ⊙ | ⊙ | * | — | — | — |
| Day 5  | ⊙ | — | ⊙ | ⊗ | ⊗ | ⊙ | — | — |
| Day 6  | ⊗ | — | ⊙ | ⊙ | ⊗ | — | ⊙ | — |
| Day 7  | ⊗ | — | ⊙ | — | ⊗ | ⊙ | — | — |
| Day 8  | ⊗ | — | — | ⊗ | ⊗ | ⊙ | — | — |
| Day 9  | ⊙ | — | — | ⊗ | ⊗ | ⊙ | ⊙ | — |
| Day 10 | ⊙ | — | — | ⊗ | ⊗ | ⊙ | ⊙ | — |
| Day 11 | ⊙ | — | — | ⊗ | ⊗ | — | — | ⊙ |
| Day 12 | ⊙ | — | — | ⊗ | ⊗ | — | — | ⊙ |
| Day 13 | ⊙ | — | — | ⊗ | ⊗ | — | — | ⊙ |
| Day 17 | * | — | — | — | * | — | — | — |

*All animals
⊗>1 animal but less than all in cohort
⊙One animal
—No animals

TABLE 7

| Day | Bacterial Count in Chinchillas Receiving Parent Strain | Bacterial Count in Chinchillas Receiving Mutant Strain |
|---|---|---|
| 3  | No detectable bacteria all but one ear dry | No detectable bacteria all ears dry |
| 7  | 3.4 E 8 (R-#2)<br>6.4 E 8 (L-#2)<br>1.3 E 7 (R-#5)<br>2.6 E 9 (L-#5)<br>3.2 E 9 (R-#1) | 1.0 E 8 (R-#6)<br>7.4 E 5 (L-#9)<br>4.0 E 6 (R-#9) |
| 12 | 8.2 E 6 (R-#2)<br>5.9 E 8 (L-#2)<br>1.1 E 9 (R-#S)<br>1.9 E 9 (L-#5) | 6.6 E 5 (R-#6)<br>1.9 E 5 (R-#8)<br>1.3 E 7 (L-#8) |

While the vaccine containing the fimbrin protein was been administered in a carrier such as Freund's adjuvant to chinchillas, other carriers, including pharmacologically acceptable carriers, are also suitable.

The fimbrin protein is also provided to the host animal by administering transformed microorganisms, which contain the fimbrin gene and express the fimbrin protein, to the host animal. Such microorganisms include mucosal pathogens such Salmonella, Mycobacterium, or Adenovirus, which preferably are attenuated. The fimbrin produced by the transformant generates a protective immune response in the host. The transformant is administered in a suitable carrier.

Adherence of fimbriated clinical NTHi isolate to human oropharyngeal cells was inhibited in a dose-dependent manner by fimbrin protein isolated from NTHi strain 1128 but was not inhibited by the 40.5 KDa NTHi outer membrane protein. Thus fimbrin protein whether isolated from NTHI such as strains 1128 or 1885, or produced by recombinant DNA techniques, are also determined to prevent or reduce adherence of NTHi to host cells thereby preventing or reducing the severity of otitis media. The fimbrin protein is administered, before or after infection with NTHi, such as by an intranasal spray comprising the fimbrin protein and a carrier.

We claim:

1. A vaccine against non-typable *Haemophilus influenzae*, to be administered in animals, comprising a transformed microbial host containing a DNA sequence encoding fimbrin protein of non-typable *Haemophilus influenzae*, said fimbrin protein comprising amino acid 22 through amino acid 359 of SEQ. ID. NO. 2, wherein said fimbrin protein is expressed in the animal, and wherein said vaccine comprises an adjuvant.

2. The vaccine of claim 1 wherein the fimbrin protein comprises amino acid 1 through amino acid 359 of SEQ. ID. NO. 2.

3. The vaccine of claim 1 wherein the microbial host is selected from the group consisting of Salmonella, Mycobacterium and Haemophilus.

4. The vaccine of claim 1 wherein the vaccine is administered subcutaneously or intranasally.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1720 base pairs
      (B) TYPE: nucleic acid
      (C) STRANDEDNESS: double (D) TOPOLOGY: circular (ii) MOLECULE TYPE: DNA (genomic)

(iv) ANTI-SENSE: NO (vi) ORIGINAL SOURCE:
        (A) ORGANISM: non-typable Haemophilus influenzae
        (B) STRAIN: 1128

(ix) FEATURE:
        (A) NAME/KEY: CDS
        (B) LOCATION: 407..1483

(xi) SEQUENCE DESCRIPTION: SEQ ID NO:1:

```
ATGTCACTGA GGATGCGATT AGACCTGGCC ACATGCTATT AACTCATTAA GCTAAAATGG      60

CAGTCTATTG ACCTAATATC TTAAGGCGTT AATGATGTCG AATTAGATTT TGAGCATTTA     120

AGAGTGTTTA TGGAGAAATG AGTCAAGAAA GTGTGTGTTT GGATGTTTTC AATAACAAAA     180

ATTCAAAGA TATGATCTTT TCAATTTTAT AGGATAATAA GCGCACTTTT GAACGTTCCT      240

TTGGGGTAAA CATAAACAAA GGAATTGAAT TTGTCAAAAG GTAGCAATGA GGCAAATTCA     300

AACCCTCGTT AAGTGAACTG TTTAGAAGAT AACTTTGATT AAAAGTTCGG TCTAAACGGG     360

AATAATTTTT TTATTACTAT TCGATGACTA AATAGAGGAC ATCAAA ATG AAA AAA        415
                                                    Met Lys Lys
                                                     1

ACT GCA ATC GCA TTA GTA GTT GCT GGC TTA GCA GCA GCT TCA GTA GCT       463
Thr Ala Ile Ala Leu Val Val Ala Gly Leu Ala Ala Ala Ser Val Ala
      5                  10                  15

CAA GCA GCT CCA CAA GAA AAT ACT TTC TAC GCT GGC GTT AAA GCT GGT       511
Gln Ala Ala Pro Gln Glu Asn Thr Phe Tyr Ala Gly Val Lys Ala Gly
 20                  25                  30                  35

CAA GGA TCT TTC CAT GAT GGT ATT AAC AAT AAT GGC GCA ATT AAA AAG       559
Gln Gly Ser Phe His Asp Gly Ile Asn Asn Asn Gly Ala Ile Lys Lys
                 40                  45                  50

GGA TTA TCA TCT AGT AAT TAT GGT TAC AGA CGC AAT ACT TTC ACT TAT       607
Gly Leu Ser Ser Ser Asn Tyr Gly Tyr Arg Arg Asn Thr Phe Thr Tyr
         55                  60                  65

GGT GTA TTT GGT GGT TAC CAA ATT TTA AAT CAA GAT AAT TTT GGT TTA       655
Gly Val Phe Gly Gly Tyr Gln Ile Leu Asn Gln Asp Asn Phe Gly Leu
     70                  75                  80

GCT GCT GAA TTA GGT TAC GAC GAT TTC GGT CGT GCA AAA CTT CGT GAA       703
Ala Ala Glu Leu Gly Tyr Asp Asp Phe Gly Arg Ala Lys Leu Arg Glu
 85                  90                  95

GCG GGA AAA CCT AAA GCT AAA CAT ACT AAC CAC GGT GCG TAC TTA AGC       751
Ala Gly Lys Pro Lys Ala Lys His Thr Asn His Gly Ala Tyr Leu Ser
100                 105                 110                 115

TTA AAA GGC AGC TAT GAA GTG TTA GAC GGT TTA GAT GTT TAT GGC AAA       799
Leu Lys Gly Ser Tyr Glu Val Leu Asp Gly Leu Asp Val Tyr Gly Lys
                 120                 125                 130

GCA GGT GTT GCT TTA GTA CGT TCT GAT TAT AAA TTT TAT GAA GAT GCA       847
Ala Gly Val Ala Leu Val Arg Ser Asp Tyr Lys Phe Tyr Glu Asp Ala
         135                 140                 145

AAC GGT ACT CGT GAC CAC AAG AAA GGT CGT CAC ACA GCA CGT GCC TCT       895
Asn Gly Thr Arg Asp His Lys Lys Gly Arg His Thr Ala Arg Ala Ser
     150                 155                 160

GGT TTA TTT GCA GTA GGT GCA GAA TAC GCA GTA TTA CCA GAA TTA GCA       943
Gly Leu Phe Ala Val Gly Ala Glu Tyr Ala Val Leu Pro Glu Leu Ala
 165                 170                 175

GTT CGT TTA GAA TAC CAA TGG CTA ACT CGC GTA GGT AAA TAC CGC CCT       991
Val Arg Leu Glu Tyr Gln Trp Leu Thr Arg Val Gly Lys Tyr Arg Pro
180                 185                 190                 195
```

-continued

```
CAA GAT AAA CCA AAT ACC GCA ATT AAC TAC AAC CCT TGG ATT GGT TGT    1039
Gln Asp Lys Pro Asn Thr Ala Ile Asn Tyr Asn Pro Trp Ile Gly Cys
            200                 205                 210

ATC AAT GCG GGT ATT TCT TAC CGT TTC GGT CAA GGC GAA GCA CCA GTT    1087
Ile Asn Ala Gly Ile Ser Tyr Arg Phe Gly Gln Gly Glu Ala Pro Val
            215                 220                 225

GTT GCA GCA CCT GAA ATG GTA AGC AAA ACT TTC AGC TTA AAT TCT GAT    1135
Val Ala Ala Pro Glu Met Val Ser Lys Thr Phe Ser Leu Asn Ser Asp
            230                 235                 240

GTA ACT TTC GCA TTT GGT AAA GCA AAC TTA AAA CCT CAA GCA CAA GCT    1183
Val Thr Phe Ala Phe Gly Lys Ala Asn Leu Lys Pro Gln Ala Gln Ala
            245                 250                 255

ACA TTA GAC AGC GTC TAT GGC GAA ATT TCA CAA GTT AAA AGT CGA AAA    1231
Thr Leu Asp Ser Val Tyr Gly Glu Ile Ser Gln Val Lys Ser Arg Lys
260                 265                 270                 275

GTA GCT GTT GCT GGT TAC ACT AAC CGT ATT GGT TCT GAC GCG TTC AAC    1279
Val Ala Val Ala Gly Tyr Thr Asn Arg Ile Gly Ser Asp Ala Phe Asn
            280                 285                 290

GTA AAA CTT TCT CAA GAA CGT GCA GAT TCA GTA GCT AAC TAC TTT GTT    1327
Val Lys Leu Ser Gln Glu Arg Ala Asp Ser Val Ala Asn Tyr Phe Val
            295                 300                 305

GCT AAA GGT GTT GCA GCA GAC GCA ATC TCA GCA ACT GGT TAC GGT GAA    1375
Ala Lys Gly Val Ala Ala Asp Ala Ile Ser Ala Thr Gly Tyr Gly Glu
            310                 315                 320

GCA AAC CCA GTA ACT GGC GCA ACT TGT GAC CAA GTT AAA GGT CGT AAA    1423
Ala Asn Pro Val Thr Gly Ala Thr Cys Asp Gln Val Lys Gly Arg Lys
            325                 330                 335

GCA CTT ATC GCT TGT CTT GCT CCA GAC CGT CGT GTA GAA ATC GCA GTA    1471
Ala Leu Ile Ala Cys Leu Ala Pro Asp Arg Arg Val Glu Ile Ala Val
340                 345                 350                 355

AAC GGT ACT AAA TAATTTTAGT CGTTTAACGA AAGATTAAAT ACAGGAAAAG        1523
Asn Gly Thr Lys

GCTTAAACTT CGGTTTAGGC CTTTTGTTTT AAACGAAACT AAAACCAAGC ATTTTAATCA  1583

AGTTTTAACT TGTGATAAAA TGCTTACCTC GTTTATTTAT AGGAAACATT ATGGAAACCT  1643

TAGACAAAAT CAAAAAGCA AATTAGTGAA AACCCCATTC TTATTTATAT GAAAGGTTCG   1703

CCAAAAGTTT CCATCCT                                                 1720

(2) INFORMATION FOR SEQ ID NO:2:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Lys Thr Ala Ile Ala Leu Val Val Ala Gly Leu Ala Ala Ala
1               5                  10                  15

Ser Val Ala Gln Ala Ala Pro Gln Glu Asn Thr Phe Tyr Ala Gly Val
                20                  25                  30

Lys Ala Gly Gln Gly Ser Phe His Asp Gly Ile Asn Asn Gly Ala
            35                  40                  45

Ile Lys Lys Gly Leu Ser Ser Ser Asn Tyr Gly Tyr Arg Arg Asn Thr
        50                  55                  60

Phe Thr Tyr Gly Val Phe Gly Gly Tyr Gln Ile Leu Asn Gln Asp Asn
65                  70                  75                  80
```

```
Phe Gly Leu Ala Ala Glu Leu Gly Tyr Asp Asp Phe Gly Arg Ala Lys
                85                  90                  95

Leu Arg Glu Ala Gly Lys Pro Lys Ala Lys His Thr Asn His Gly Ala
            100                 105                 110

Tyr Leu Ser Leu Lys Gly Ser Tyr Glu Val Leu Asp Gly Leu Asp Val
            115                 120                 125

Tyr Gly Lys Ala Gly Val Ala Leu Val Arg Ser Asp Tyr Lys Phe Tyr
            130                 135                 140

Glu Asp Ala Asn Gly Thr Arg Asp His Lys Lys Gly Arg His Thr Ala
145                 150                 155                 160

Arg Ala Ser Gly Leu Phe Ala Val Gly Ala Glu Tyr Ala Val Leu Pro
                165                 170                 175

Glu Leu Ala Val Arg Leu Glu Tyr Gln Trp Leu Thr Arg Val Gly Lys
                180                 185                 190

Tyr Arg Pro Gln Asp Lys Pro Asn Thr Ala Ile Asn Tyr Asn Pro Trp
            195                 200                 205

Ile Gly Cys Ile Asn Ala Gly Ile Ser Tyr Arg Phe Gly Gln Gly Glu
            210                 215                 220

Ala Pro Val Val Ala Ala Pro Glu Met Val Ser Lys Thr Phe Ser Leu
225                 230                 235                 240

Asn Ser Asp Val Thr Phe Ala Phe Gly Lys Ala Asn Leu Lys Pro Gln
                245                 250                 255

Ala Gln Ala Thr Leu Asp Ser Val Tyr Gly Glu Ile Ser Gln Val Lys
                260                 265                 270

Ser Arg Lys Val Ala Val Ala Gly Tyr Thr Asn Arg Ile Gly Ser Asp
            275                 280                 285

Ala Phe Asn Val Lys Leu Ser Gln Glu Arg Ala Asp Ser Val Ala Asn
290                 295                 300

Tyr Phe Val Ala Lys Gly Val Ala Ala Asp Ala Ile Ser Ala Thr Gly
305                 310                 315                 320

Tyr Gly Glu Ala Asn Pro Val Thr Gly Ala Thr Cys Asp Gln Val Lys
                325                 330                 335

Gly Arg Lys Ala Leu Ile Ala Cys Leu Ala Pro Asp Arg Arg Val Glu
                340                 345                 350

Ile Ala Val Asn Gly Thr Lys
            355

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Pro Gln Glu Asn Thr Phe Tyr Ala Gly Val Lys Ala Gly Gln Gly
1               5                   10                  15

Ser Phe His Asp
            20

(2) INFORMATION FOR SEQ ID NO:4:

(i) SEQUENCE CHARACTERISTICS:
        (A) LENGTH: 15 amino acids
        (B) TYPE: amino acid
```

```
            (C) STRANDEDNESS: single
            (D) TOPOLOGY: linear (ii) MOLECULE TYPE: peptide (xi) SEQUENCE DESCRIPTION: SEQ ID NO:4:

Val Ser Lys Thr Phe Ser Leu Asn Ser Asp Val Thr Phe Ala Phe
1               5                   10                  15

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iv) ANTI-SENSE: NO (xi) SEQUENCE DESCRIPTION: SEQ ID NO:5:

CARGARAACA CNTTCTAYGC                                                   20

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

AAANGCRANG TNACRTC                                                      17
```